US006624341B1

(12) United States Patent
Depner et al.

(10) Patent No.: US 6,624,341 B1
(45) Date of Patent: Sep. 23, 2003

(54) BREATHABLE BACKSHEET DESIGN FOR DISPOSABLE ABSORBENT ARTICLES

(75) Inventors: Michael Depner, Mainz (DE); Michael Divo, Friedrichsdorf (DE)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 08/836,556

(22) PCT Filed: Oct. 16, 1995

(86) PCT No.: PCT/US95/13544

§ 371 (c)(1),
(2), (4) Date: Oct. 16, 2000

(87) PCT Pub. No.: WO96/14034

PCT Pub. Date: May 17, 1996

(30) Foreign Application Priority Data

Nov. 5, 1994 (EP) .............................................. 94203228

(51) Int. Cl.[7] ................................................. A61F 13/15
(52) U.S. Cl. ....................................... 604/367; 604/383
(58) Field of Search ................................ 604/367–370, 604/383

(56) References Cited

U.S. PATENT DOCUMENTS

| 3,881,489 | A | * | 5/1975 | Hartwell | ..................... 604/369 |
| 4,341,216 | A | | 7/1982 | Obenour | ..................... 128/287 |
| 4,591,523 | A | | 5/1986 | Thompson | ................... 428/131 |
| 4,950,264 | A | | 8/1990 | Osborn, III | .............. 604/385.1 |
| 5,366,453 | A | * | 11/1994 | Zehner et al. | .......... 604/385.29 |
| 6,316,687 | B1 | * | 11/2001 | Davis et al. | ................ 604/372 |

OTHER PUBLICATIONS

Copy of International Search Report dated Mar. 19, 1996.

* cited by examiner

Primary Examiner—Weilun Lo
Assistant Examiner—Jamisue A Webb
(74) Attorney, Agent, or Firm—Jay A. Krebs; Ken K. Patel

(57) ABSTRACT

The present invention relates to disposable absorbent articles such as baby diapers or sanitary napkins having a breathable yet liquid leakage retarding backsheet which comprises an inner and an outer layer. The inner layer being closer to the absorbent structure of the article is a formed film with directional liquid transport characteristics while the outer layer is a fibrous fabric.

15 Claims, No Drawings

BREATHABLE BACKSHEET DESIGN FOR DISPOSABLE ABSORBENT ARTICLES

FIELD OF THE INVENTION

The present invention relates to disposable absorbent articles such as baby diapers or sanitary napkins having a breathable yet liquid leakage retarding backsheet which comprises an inner and an outer layer. The inner layer being closer to the absorbent structure of the article is a formed film with directional liquid transport characteristics while the outer layer is a fibrous fabric.

BACKGROUND OF THE INVENTION

Disposable absorbent articles such as baby diapers, adult incontinence products, sanitary napkins and panty liners are well known in the art. These articles have a wearer facing side through which they typically absorb liquids discharged by the wearer. The liquid is stored in an absorbent structure. Liquid leakage from the article through the surface opposite the wearer facing side is usually prevented by incorporating a liquid impermeable backsheet on that side.

It is also well established in the art that a backsheet allowing gaseous fluid (air) communication with the environment, usually referred to as breathability, is highly desirable. Breathability improves with the amount of air permeating through a backsheet. This amount is proportional to the open area (the sum of the area of all apertures) in the backsheet. Obviously too many and particularly too large apertures in the backsheet lead to compromising the liquid leakage prevention, which is the primary function of a backsheet.

Many suggestions how to provide breathable backsheets have been recorded in the art. Numeral attempts of combining the mutual contradicting features of gas permeability and liquid impermeability have been documented in patents and patent applications. However the lack of commercially available breathable disposable absorbent articles indicates that the technology so far suggested has not provided an all around satisfactory result for the desired technical requirements at commercially acceptable condition. More often than not satisfaction of one desired feature went to such an extreme that the respective other feature was not properly satisfied any longer.

For example sanitary napkins with very high breathability at the cost of frequent liquid leakage (leading to soiling of the undergarments of a wearer) cannot be considered satisfactory. On the other hand satisfying the liquid leakage problem properly usually resulted in almost impermeable, that is non-breathable, backsheets. In particular microporous films which have no macroscopic apertures are not liquid permeable. But microporous films only allow air communication by diffusion which is an order of magnitude less than the achieved breathability with the current invention.

Good progress has been made in the field of formed films having directional liquid transport wherein liquid transport over a certain pressure drop across a formed film is better in one direction versus the other. These so called one way formed film materials have found wide usage as liquid permeable topsheets after being treated with surfactant in the field of sanitary napkins and panty liners, but also for diapers and incontinence products. Alternative topsheets of fibrous fabric polymers typically have no directional liquid transport. They are also treated with surfactant but have an intrinsic hydrophobic behaviour when being used as topsheets for absorbent articles after the surfactant has worn off.

Combinations of breathable and liquid permeable sheets in order to provide a certain liquid impermeability while satisfying the desire for breathable backsheets have already been suggested for example in U.S. Pat. No. 3,881,489. In this disclosure a breathable backsheet is provided by confining an outer layer of formed film material having surface aberrations with apertures therein and an inner layer of a paper tissue having a high void volume and having been made hydrophobic by impregnating it with a paraffin wax. This document does not disclose the desire for using a directional liquid transport type polymeric film structure with a hydrophobic fibrous fabric layer made of polymeric material.

Other prior art attempts to provide breathable backsheet assemblies comprising more than one layer are e.g. documented in U.S. Pat. No. 4,341,216, EP-A-109 126 or EP-A-203 821. Neither of these disclosures provides constructions of breathable backsheets similar to the present invention.

Single layer breathable backsheets are known for example from GB-A-2184391, GB-A-2184390, GB-A-2184389, U.S. Pat. Nos. 4,591,523, 4,839,216 or EP 156471.

In PCT publication WO 9309744 absorbent articles which have a hybrid topsheet are disclosed. The hybrid topsheet comprises a non-woven fabric overlaid by a formed film were the non-woven fabric is folded around the edges but not fully covering the second surface of the formed film. This structure is used as the topsheet to facilitate a liquid absorption in contrast to breathability. However it would of course provide breathability if it was left in air communication with the environment. This disclosure teaches to use the structure as a topsheet which is typically rendered hydrophilic. Further the disclosed topsheet structure has a formed film outer layer and a non-woven inner layer in respect to the absorbent structure. Therefore this publication also does not disclose the structures according to the present invention.

In unpublished, pending applications U.S. Ser. Nos. 08/042,364; 08/042,365 and 08/042,345 all filed on Feb. 4, 1993 other topsheets comprising a formed film and non woven fabric are disclosed. However these constructions are rendered hydrophilic for the purpose of using them as topsheets receiving liquid to be transported towards the absorbent core rather than to use them on breathable backsheets.

It has now been found that combining a gas permeable, hydrophobic, polymeric fibrous fabric and an apertured formed film having a directional liquid transport phenomena provides a particularly desirable breathable backsheet. Backsheets according to this construction have exceptionally good breathability due to the large open area and the combination of formed film and fibrous fabric allows to select the layers so as to provide the desired liquid leakage retarding function. Therefore the present invention provides an non-leaking breathable backsheet and absorbent articles comprising this backsheet.

It is therefore an objective of the present invention to provide absorbent articles in particular sanitary napkins or panty liners having a superior breathability as defined by free gas permeability of the backsheet while simultaneously retarding liquid leakage through that backsheet to such an extend that the user of such products does not experience a recognisable difference between a liquid impermeable backsheet and the breathable backsheet according to the present invention.

An additional objective satisfied by the present invention is also to provide a backsheet which has a desirable and user preferred fibrous outside surface.

CROSS REFERENCE

Another patent application is being filed on the same date as this application. It is entitled "Breathable dual layer backsheet design for disposable absorbent articles" by M. Depner and M. Divo and also assigned to "The Procter and Gamble Company".

DESCRIPTION OF THE INVENTION

The present invention relates to breathable absorbent articles such as baby diapers, adult incontinence products, sanitary napkins or panty liners. Typically such products have a topsheet, a backsheet and an absorbent core between the topsheet and the backsheet. The articles according to the present invention have a breathable backsheet comprising an inner layer and an outer layer where the inner layer is closer to the absorbent core than the outer layer. The outer layer comprises a hydrophobic, gas permeable fibrous fabric layer composed of polymeric fibres such as polymeric non-wovens well known in the art of absorbent articles.

The inner layer comprises a hydrophobic gas-permeable apertured polymeric film having a directional liquid transport phenomena. The film has a first and a second liquid transport direction which are opposite to each other. The first liquid transport direction is from the outer layer towards the absorbent core. Liquid transport in the first direction is larger than liquid transport in the second direction when measured under an identical pressure drop across the apertured film.

It is preferred that the breathable backsheet of the absorbent article provides a threshold pressure below which a test liquid does not permeate in the second liquid transport direction through the backsheet, thereby providing a "zero leakage" threshold. This threshold will be dependent on the usage circumstances of the product, e.g. babies will not provide a pressure onto their diaper when sitting as large as women onto their panty liners when bicycling.

For sanitary napkins or panty liners the respective pressure threshold has been found to be equivalent to 45 g/cm$^2$ (i.e. 4414.5 Pa.) according to the test protocol disclosed in the example below. The test liquid used to identify test leakage comprises a saline solution consisting of 2 g urea, 0.9 g sodium chloride, 0.06 g calcium chloride and 0.11 g hydrated magnesium sulphate in 100 ml distilled water. This solution is adjusted for surface tension by adding surfactant to better simulate bodily discharges other than urine. The reduced surface tension of the solution 29+/−1 mN/m while the saline solution without surfactant has a surface tension of more than 60 mN/m.

The fibrous fabric layer of the outer layer preferably has a basis weight of 10 to 100 g/m$^2$ preferably 15 to 30 g/m$^2$. The fibres can be made of any hydrophobic polymeric material usual in the art of making fibrous fabric layers. Depending on the circumstances of the ultimate use and manufacturing of the breathable absorbent article fibres of polyethylene, polypropylene, polyester, polyacetat or combinations thereof (intra- and inter-fibres combinations) have been found useful. The fibres are preferably spunbonded, carded or melt blown. The fabric layer most preferably comprises a matrix of spunbonded fibres covered on one or both sides with meltblown fibres but can also be provided by any other typical technology used in the art.

The apertured film according to the present invention can be any of those well known in the art. This includes in particular, but is not limited to those films disclosed in U.S. Pat Nos. 3,929,135, 4,151,240, 4,319,868, 4,324,426, 4,342,314 and 4,591,523.

The apertured film comprised in the inner layer of the breathable backsheet preferably has funnel shaped apertures similar to those described e.g. in U.S. Pat. No. 3,929,135. The apertures maybe circular or non-circular but have a cross sectional dimension at one end of the funnel which is wider than the opening at the other end of the funnel. The direction from the larger funnel opening towards the smaller opening is of course parallel to the first liquid transport direction. The open area of the apertured film is typically more than 5%, preferably in the range of 10% to 35% of the total film surface. The apertured films can be made of any material typical in the art but preferably is made of a polymer similar to those used for the fibrous fabric layer.

The minimum hydraulic diameter of the apertures in the film should be as small as possible while still providing sufficient gas permeability without hydraulic blockage of the apertures. A hydraulic diameter of as little as 0.2 mm, preferably 0.3 to 0.7 mm has been found possible in the context of the present invention. Hydraulic diameter for non circular apertures is the diameter that a circular aperture with the same cross section would have. Diameter is always determined in the plane of smallest cross section of an aperture.

In particularly preferred embodiments of the present invention the layers of the breathable backsheet are joined to each other across less than the total area which is coextensive with the absorbent core. Particularly inner and outer layers which are unattached across half of the area, most preferably across the total area which is coextensive with absorbent core have been found beneficial to leakage prevention without breathability reduction. Of course the outer layer and inner layer of the backsheet need to be combined somewhere to create the breathable backsheet combination of the present invention. This combining can for example be provided in the periphery outside the area coextensive with the absorbent core or in a pattern of lines or dots across the whole area coextensive with the absorbent core which pattern does not cover any significant area itself.

The present invention as indicated above can be used beneficially in the context of many different absorbent articles. However sanitary napkins and especially thin panty liners are particularly susceptible to the present invention. Sanitary napkins or panty liners having a thickness of 3 mm or less and preferably 2 mm or less benefit especially well from the breathable backsheet of the present invention.

The disposable absorbent articles according to the present invention can have all those other features and parts which are typical for products in the context of their intended use. They comprise typically the absorbent structure which can be a fluffy fibrous absorbent core comprising also hydrogel particles if desired, laminated tissues with or without particulate materials including hydrogel particles or odour control particles. The absorbent core fibres can be any of those known in the art including cellulose fibres or polymeric fibres rendered absorbent or even non-absorbent matrix fibres. Also tissues of sufficient basis weight and absorbency can be used as the absorbent structure according to the present invention. E.g. the tissue used in the method described below to measure wet-through can be used in the context panty liners.

Also a topsheet or wearer contacting layer through which the liquids to be absorbed penetrate to the absorbent structure is typically incorporated in articles according to the present invention. The topsheet or wearer contacting layer can be provided by any of those materials and techniques known in the art including formed films and non-woven fibrous fabrics similar to those described herein above.

EXAMPLES

For testing the following examples the wet-through method as described below was used. It follows conceptually the wet-through method disclosed in U.S. Pat. No. 3,881,489 but relates to the backsheet wet-through prevention ability.

Test Preparation

The breathable backsheet to be analysed is provided with a generally hydrophilic, test liquid absorbing tissue on the inside surface. The tissue is placed without exerting pressure on the backsheet. Then samples of 5 cm times 5 cm are cut and compressed under a load of 40 g/cm$^2$ (or 1.0 kg per sample). Not required for the test but desirable for easy operation of the test is an additional layer of non woven fabric, or formed film on top of the absorbent tissue.

For repeatability the samples are kept for at least 4 hours at test conditions. Test conditions are 23° C. and 50% relative humidity. The test liquid is prepared by mixing 100 ml of distilled water, 2 g urea, 0.9 g NaCl, 0.11 g MgSO$_4$×7 H$_2$O and 0.06 g CaCl$_2$. The test liquid then is adjusted to a surface tension of 29+/−1 mN/m to resemble particularly the condition exhibited by women with vaginal discharge. To resemble other discharges the surface tension can be kept unaltered at about 60 mN/m.

Test Materials

Typical test materials are e.g. a tissue designated 609912, of 99 g/m$^2$ obtainable from the Merfin Hygienic Products company, in Delta, B.C., Canada. Generally the tissue should be not thicker than 1 mm.

The blotter paper can be any good absorbent blotter paper commercially available. For the tests below blotter paper designated Absorbent bianco No 30 (220 g/m$^2$) of Cartiera, Favini in 36028 Rossano Veneto (VC), Italy was used. The blotter paper can be cut into larger areas than the 5 cm×5 cm sample size.

The desirable non-woven or formed film shall not be absorbent and shall have no surface residue wash-off which would alter the test liquid composition. This can be achieved by washing the material with test liquid and drying it prior to it's use.

Test Liquid Quantity

The test liquid quantity to be used in the test is determined as the amount necessary to saturate the absorbent tissue. This can be determined by preparing tissue samples of 5 cm×5 cm, preferably larger but with a known surface area, of the tissue to be used in the wet-through test. The weight of the tissue sample is determined.

The tissue is then placed on a nylon net having rectangular and diagonal running threads stretched inside a frame. The net forms rectangles of 5 cm×4.5 cm which are split into 4 equal parts by threads connecting the corners diagonally. The frame is preferably of a water repellent material such as a hydrophobic polymer.

The net together with the tissue samples are then immersed in destilled water of 23° C. (+/−1° C.) for 30 seconds (+/−3 seconds). Then the net together with the tissue is left to drain/drip in a horizontal position only under gravitational forces for 120 seconds (+/−5 seconds). Then the weight of the tissue together with the absorbed water is measured. The scales for the weight measurements should be accurate to 0.1 gram.

The amount of absorbed water is calculated (wet weight minus dry weight) and divided by the surface area of the tissue sample. This value is multiplied by the surface area of 25 cm$^2$ of the wet-through test samples (5 cm×5 cm) to result in the test liquid quantity to be used. Statistical analysis should be used to ensure an accuracy of +/−10% of the test liquid quantity value within a +/−3 Sigma range of the test series (adjusted for surface area of 25 cm$^2$.

Test Method to Determine Wet-through at Defined Load

The samples are placed on an absorbent blotter paper with the breathable backsheet adjacent the blotter paper. The size of the blotter paper should be larger than the test sample size. The blotter paper is conditioned as the test samples are and its weight prior to the test is taken.

Then the defined test liquid quantity is placed in the centre of the sample. The flow rate when placing the liquid should be about 1 ml/10 sec., i.e. the test liquid should be placed onto the sample in about 20 sec. for 2 ml loadings. After 2 minutes a load of 40 g/cm$^2$ is applied to the wet sample for 15 seconds. Typically the minimum load is 20 g/cm$^2$ or 0.5 kg per sample, however for simulating a stress condition a load of 40 g/cm$^2$ is applied. After removal of the load the blotter paper is checked for wet-through.

If there is wet-through the occurrence is noted as qualitative result or the weight of the blotter paper with the leaked absorbent liquid which has been absorbed is measured. The difference of the second measurement to the original dry weight of the blotter paper is the amount of wet-through which provides a quantitative result.

Care must be taken to not introduce side leakage e.g. due to an uneven liquid migration from the centre of the sample. The samples must be stored horizontally during the test. If side leakage occurs anyway at the edges of the sample and wet trough is observed the quantitative amount of wet-through outside the sample area is to be disregarded. If all test samples have side edge leakage without wet-through occurring a different tissue should be used to confirm the test result. If the result is consistent then the qualitative and quantitative results are no wet-through.

Results

At least 10 samples should be measured and averaged. Statistical analysis should be used to confirm that the average result is statistically correct within a 95% confidence interval.

Test Method to Determine Wet-through Threshold Load

This method is identical to the test method at constant load except that the load starting from 20 g/cm2 is gradually increased by increments of 5 g/cm$^2$ (125 g per sample). The measurement of wet-through quantity is not required but the test person needs to determine the lowest load at which wet-through occurs. The threshold load is defined as the lowest load at which wet-through occurs minus 5 g/cm$^2$. If wet-through occurs at 20 g/cm$^2$ already the breathable backsheet is reported to be leaking without threshold load.

Test Products

Backsheets according to the present invention were constructed from the following raw material:

non-woven fabric of 28 g/m$^2$ having a spunbonded layer of 14 g/m$^2$ and a melt blown layer of 14 g/m$^2$ obtainable from Corovin GmbH, Peine, Germany under the designation MD 2000.

polyethylene formed film according to U.S. Pat. No. 3,929,135 obtainable from Tredegar Film Products B.V., Kerkrade, The Netherlands. The film has circular funnel shaped apertures with an open area of 19%, an embossed thickness of 0.48 mm (funnel height) and an aperture diameter of 0.465 mm.

The backsheet according to the invention is prepared by joining the film with the funnels pointing towards the absorbent structure (for this testing the absorbent structure was the 99 g/m$^2$ Merfin tissue described supra) and the fabric with the melt blown layer being oriented to become the inter face between formed film and fabric.

In an example according to the present invention the fabric and the film are overlaying each other without attaching the two layers. The test liquid was used at 2 ml per sample.

Threshold Pressure Test with Reduced Surface Tension Test Liquid

| First leakage observed at | 50 g/cm² |
|---|---|
| Threshold pressure | 45 g/cm² |

Wet/through Test

Wet/through qualitative test were conducted at 40 g/cm² and 220 g/cm² with test liquid (surface tension 29 mN/m) and test liquid without surfactant (surface tension 62 mN/m). The results provide a valuable display of the synergistic effect of the breathable structure according to the present invention. In the table below "Y" indicates wet-through occurrence (quantitative result in % of test liquid in brackets) while "N" indicates no wet-through (0%).

| Load | 40 g/cm² | 220 g/cm² |
|---|---|---|
| surface tension 62 mN/m (test liquid without surfactant) | | |
| example according to the present invention film with funnels | N | N |
| | N | Y (14.5%) |
| fabric with melt blown layer | N | N |
| surface tension 29 mN/m (test liquid with surfactant) | | |
| example according to the present invention | N | Y (<50%) |
| film with funnels | N | Y (>50%) |
| fabric with melt blown layer | Y (35%) | Y (>50%) |

What is claimed is:

1. Breathable absorbent article comprising a topsheet, a breathable backsheet and an absorbent core between said topsheet and said backsheet, said backsheet comprising an inner layer and an outer layer, said inner layer being closer to said absorbent core than said outer layer, said article being characterised in that said outer layer comprises a hydrophobic, gas-permeable fibrous fabric layer composed of polymeric fibres and said inner layer comprises a hydrophobic, gas-permeable apertured polymeric film, said apertured film having a first liquid transport direction and a second liquid transport direction opposite said first liquid transport direction, said inner layer being oriented such that said first direction is from said outer layer towards said absorbent core, said apertured film allowing a liquid transport in said first liquid transport direction which is larger than the liquid transport in said second liquid transport direction under an identical pressure drop across said apertured film.

2. Breathable absorbent article according to claim 1 wherein said article is a sanitary napkin or panty liner having a thickness of 3 mm or less.

3. Breathable absorbent article according to claim 2 wherein said breathable backsheet has no liquid transport in said second direction under a pressure of a load of 45 g/cm² or less for an aqueous saline solution consisting of 100 ml distilled water, 2 g urea, 0.9. g NaCl, 0.11 g MgSo₄×7H₂O, 0.06 g CaCl₂, the saline solution is adjusted with surfactant to 29+/−1 mN/m.

4. Breathable absorbent article according to claim 2 wherein said article is a sanitary napkin or panty liner having a thickness of 2 mm or less.

5. Breathable absorbent article according to claim 1 wherein said fibrous fabric layer is made of fibres of polyethylene, polypropylene, polyester, polyacetate or combinations thereof and preferably said fabric layer comprises a matrix of spunbonded fibres covered on one or both sides with meltblown fibres.

6. Breathable absorbent article according to claim 1 wherein said apertured film comprises funnel shaped apertures wherein the direction from the larger funnel opening towards the smaller opening is parallel to said first liquid transport direction.

7. Breathable absorbent article according to claim 1 wherein said apertured film has an open area of more than 5%, of the film's total surface.

8. Breathable absorbent article according to claim 7 wherein said apertured film has an open area in the range of 10% to 35% of the total film surface.

9. Breathable absorbent article according to claim 1 wherein said inner layer and said outer layer, across at least 50% of the area which is coextensive with said absorbent core, are not attached to each other.

10. Breathable absorbent article according to claim 9 wherein said inner layer and said outer layer, across at least 90% of the area which is coextensive with said absorbent core, are not attached to each other.

11. Breathable absorbent article according to claim 1 wherein said fibrous fabric layer has a basis weight in the range of 10 to 100 g/m².

12. Breathable absorbent article according to claim 11 wherein said fibrous fabric layer has a basis weight in the range of 15 to 30 g/m².

13. Breathable absorbent article according to claim 1 wherein said apertured film has apertures with a minimum hydraulic diameter of 0.2 mm.

14. Breathable absorbent article according to claim 13 wherein said apertured film has apertures with a minimum hydraulic diameter in the range of 0.3 mm to 0.7 mm.

15. Breathable absorbent article according to claim 1 wherein said inner layer and said outer layer, across the whole area which is coextensive with said absorbent core, are not attached to each other.

* * * * *